(12) United States Patent
Kramer et al.

(10) Patent No.: US 11,295,634 B2
(45) Date of Patent: Apr. 5, 2022

(54) REALISTIC ELECTRO-ANATOMICAL MODEL OF THE MAMMALIAN HIS/PURKINJE SYSTEM

(71) Applicant: St. Jude Medical, Cardiology Division, Inc., St. Paul, MN (US)

(72) Inventors: Scott A. Kramer, Minneapolis, MN (US); Paul A. Belk, Maple Grove, MN (US); Juan Carlos Tantalean, II, Fridley, MN (US); Gavin P. Seeker, Maple Grove, MN (US); Patrick P. Senarith, Maple Grove, MN (US); Erich W. Stoermer, Plymouth, MN (US); David J. Broman, Rogers, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 743 days.

(21) Appl. No.: 16/208,348

(22) Filed: Dec. 3, 2018

(65) Prior Publication Data

US 2019/0172372 A1 Jun. 6, 2019

Related U.S. Application Data

(60) Provisional application No. 62/598,518, filed on Dec. 14, 2017, provisional application No. 62/594,130, filed on Dec. 4, 2017.

(51) Int. Cl.
*G09B 23/30* (2006.01)
*A61B 34/10* (2016.01)
(Continued)

(52) U.S. Cl.
CPC .............. *G09B 23/30* (2013.01); *A61B 34/10* (2016.02); *A61N 1/365* (2013.01);
(Continued)

(58) Field of Classification Search
CPC ... G09B 23/28; G09B 23/23285; G09B 23/30
See application file for complete search history.

(56) References Cited

U.S. PATENT DOCUMENTS

| 3,688,008 A | * | 8/1972 | Krieger, Sr. | ........... G09B 23/30 434/268 |
| 4,639,223 A | * | 1/1987 | Keller, Jr. | .............. G09B 23/28 434/272 |

(Continued)

*Primary Examiner* — Kurt Fernstrom
(74) *Attorney, Agent, or Firm* — Lerner, David, Littenberg, Krumholz & Mentlik, LLP

(57) ABSTRACT

An electro-anatomical model of the mammalian His/Purkinje system includes a shell simulating the anatomy of at least a portion of a mammalian heart. The shell has a hollow interior and a first port providing an aperture to the interior of the shell. A plug is inserted in the first port so that a surface of the plug is exposed to the interior of the shell. An electrical circuit provides signals to electrodes in the plug which simulate the electrical signals generated by the bundle of His/Purkinje system in vivo. A second port provides access to the interior of the shell for an introducer catheter to locate the simulated bundle of His and to insert a pacing lead therein. The model is useful for developing tools for His pacing and for training users in techniques for implanting His pacing leads.

20 Claims, 8 Drawing Sheets

(51) Int. Cl.
  *A61N 1/365* (2006.01)
  *A61B 18/00* (2006.01)
  *A61B 17/00* (2006.01)
  *A61N 1/05* (2006.01)

(52) U.S. Cl.
  CPC .......... *A61B 2017/00053* (2013.01); *A61B 2018/00351* (2013.01); *A61B 2034/105* (2016.02); *A61N 1/056* (2013.01)

(56) References Cited

U.S. PATENT DOCUMENTS

| | | | | |
|---|---|---|---|---|
| 5,482,472 | A * | 1/1996 | Garoni | G09B 23/30 |
| | | | | 345/83 |
| 6,773,263 | B2 * | 8/2004 | Nicholls | G09B 23/30 |
| | | | | 434/267 |
| 8,834,172 | B2 * | 9/2014 | Rubinstein | G09B 23/30 |
| | | | | 434/267 |
| 9,183,763 | B2 * | 11/2015 | Carson | G09B 23/281 |
| 9,463,072 | B2 * | 10/2016 | Comaniciu | G16H 50/50 |
| 9,773,347 | B2 * | 9/2017 | Groth | G09B 23/34 |
| 10,037,715 | B2 * | 7/2018 | Toly | G09B 23/28 |
| 10,229,615 | B2 * | 3/2019 | Carson | G09B 23/32 |
| 10,311,978 | B2 * | 6/2019 | Mansi | G06F 30/20 |
| 10,769,966 | B2 * | 9/2020 | Sebro | G09B 23/30 |
| 2013/0196301 | A1 * | 8/2013 | Carson | G09B 23/303 |
| | | | | 434/265 |

* cited by examiner

REALISTIC ELECTRO-ANATOMICAL MODEL OF THE MAMMALIAN HIS/PURKINJE SYSTEM

CROSS-REFERENCE TO RELATED APPLICATIONS

The present application claims the benefit of the filing dates of United States Provisional Patent Application Nos. 62/594,130, filed Dec. 4, 2017, and 62/598,518, filed Dec. 14, 2017, the disclosures of which are hereby incorporated by reference herein.

FIELD OF THE DISCLOSURE

The present disclosure relates to cardiac resynchronization therapy (CRT), and more particularly to pacing of the His bundle in the heart of a patient. Still more particularly, the present invention relates to an anatomical model for facilitating the development of tools for use in His pacing, as well as for training users in techniques for implanting His pacing leads in patients.

BACKGROUND OF THE DISCLOSURE

Cardiac rhythm management systems are useful for electrically stimulating a patient's heart to treat various cardiac arrhythmias. The current standard of care is to pace the right ventricle by myocardial stimulation. In this technique, pacemaker leads are fixed directly into the right ventricular myocardium, possibly with another lead fixed in a left coronary vein. Electrical pulses are transmitted from a pacemaker through one or both leads, resulting in focal stimulation of the ventricular muscle. While effective, this technique can cause abnormal electrical activation sequences resulting in mechanical ventricular dyssynchrony and an increased risk of heart failure, atrial fibrillation and overall mortality.

There is growing interest in pacing the human ventricles by direct stimulation of the specialized ventricular conduction (His/Purkinje) system. This approach involves the placement of an electrode lead into the bundle of His located either in the septal wall of the right atrium or subvalvular from the right ventricle also in the atrial septum. As part of the electrical conduction system of the heart, the bundle of His transmits electrical impulses from the atrioventricular (AV) node to the ventricles of the heart. As the electrical impulses that regulate the heartbeat are conducted through the bundle of His from the right atrium to the left and right ventricles, a lead placed in or in close proximity to the bundle of His would enable the entire electrical conduction system to be paced in a physiologically natural way. Pacing the ventricles in this manner, which closely mimics normal AV conduction, can greatly reduce or eliminate the risks associated with traditional CRT pacing.

While the improved results obtainable with His pacing have been recognized, in practice His pacing is difficult to achieve because the bundle of His is very small and difficult to locate and access with available pacing tools. The bundle of His has a nominal length of about 5 mm and a nominal width of about 2 mm. It generates an electrical signal that is a small fraction of that generated by the ventricles. As a result of its small size and weak electrical signal, the bundle of His is extremely difficult to find with a conventional pacing lead. Moreover, once the bundle of His has been located, it is difficult to maintain the position of the lead while it is being affixed to the cardiac tissue. The difficulties involved in locating the bundle of His and affixing a pacing lead thereto result in lengthy implantation procedures.

The foregoing difficulties could be minimized by the development of improved tools for delivering and implanting electrode leads, and by improved training of users in techniques for implanting His pacing leads. Both attempts to develop tools for His pacing, and the training of users in techniques for implanting His pacing leads, have been limited by the inadequacy of development models. Models with approximately appropriate anatomy and physiology have been limited to large mammals such as pigs or dogs. The use of these models is hindered by inconvenience, both in terms of expense and the inability to see directly where the lead is going, and by significant anatomic and physiologic differences between the best available animal models and humans.

There therefore is a need for a model that accurately represents relevant cardiac anatomy, both human and animal, approximates tissue properties near the bundle of His, and simulates relevant electrical anatomy. Such a model preferably would allow rapid prototyping of clinical tools to facilitate His pacing, and would also allow high-quality, convenient and inexpensive training of users to implant His pacing leads.

BRIEF SUMMARY OF THE DISCLOSURE

The model comprises a preferably anatomically-accurate representation of the relevant sections of the right atrium and/or right ventricle of a human or animal, represented as an at least partially hollow, and at least partially transparent, shell. A non-transparent shell is also contemplated. The region in which the bundle of His is located is simulated by a conductive insert. The insert allows fixation of at least one lead and, in one embodiment, has physical and/or electrical properties that simulate myocardial tissue. In some embodiments, the insert may be doped with an ionic material to provide electrical properties similar to the bundle of His so electrically-active catheters can be used to map the region, as is done in clinical practice. The insert may be contoured using a customized cap to ensure that the interface between the shell and the insert is not palpable during model use. In use, the insert may be stimulated electrically by a circuit to produce an electrical signal and preferably a signal very similar to the signal produced by the bundle of His.

Thus, one aspect of the present disclosure provides an electro-anatomical model of the mammalian His/Purkinje system. The model includes a base; a shell mounted to the base and simulating the anatomy of at least a portion of a mammalian heart, the shell having a hollow interior; a first port providing an aperture to the interior of the shell; a plug inserted in the first port, the plug having a surface exposed to the interior of the shell; and a circuit providing electrical signals to the plug to simulate electrical signals generated by the bundle of His/Purkinje system in vivo.

Also contemplated are methods of producing and using this His model. In particular, another aspect of the present disclosure provides a method for simulating the delivery of a pacing lead to the His bundle of a patient's heart. The method includes providing an electro-anatomical model simulating the anatomy of at least a portion of a mammalian heart, the model including a shell with a hollow interior, first and second ports providing apertures to the interior of the shell, and a plug inserted in the first port, the plug having a face exposed to the interior of the shell; transmitting electrical signals to the plug to simulate electrical signals generated by the bundle of His/Purkinje system in vivo;

providing an introducer catheter having a sheath with an axial lumen, a distal end, an electrode at the distal end, and a pacing lead disposed in the axial lumen; inserting the introducer catheter through the second port to the interior of the shell until the distal end of the sheath confronts the exposed face of the plug; moving the distal end of the sheath relative to the exposed face of the plug until the electrode at the distal end of the sheath receives at least a portion of the electrical signals transmitted to the plug; and deploying the pacing lead from the axial lumen of the sheath and implanting the pacing lead in the exposed face of the plug.

Also contemplated is a heart pacing device or mapping device which electrically interfaces with the His/Purkinje cells or systems tested using the model of the disclosure.

BRIEF DESCRIPTION OF THE DRAWINGS

A more complete appreciation of the subject matter of the present disclosure and the various advantages thereof can be realized by reference to the following detailed description in which reference is made to the accompanying drawings in which.

DETAILED DESCRIPTION

Figure 1:
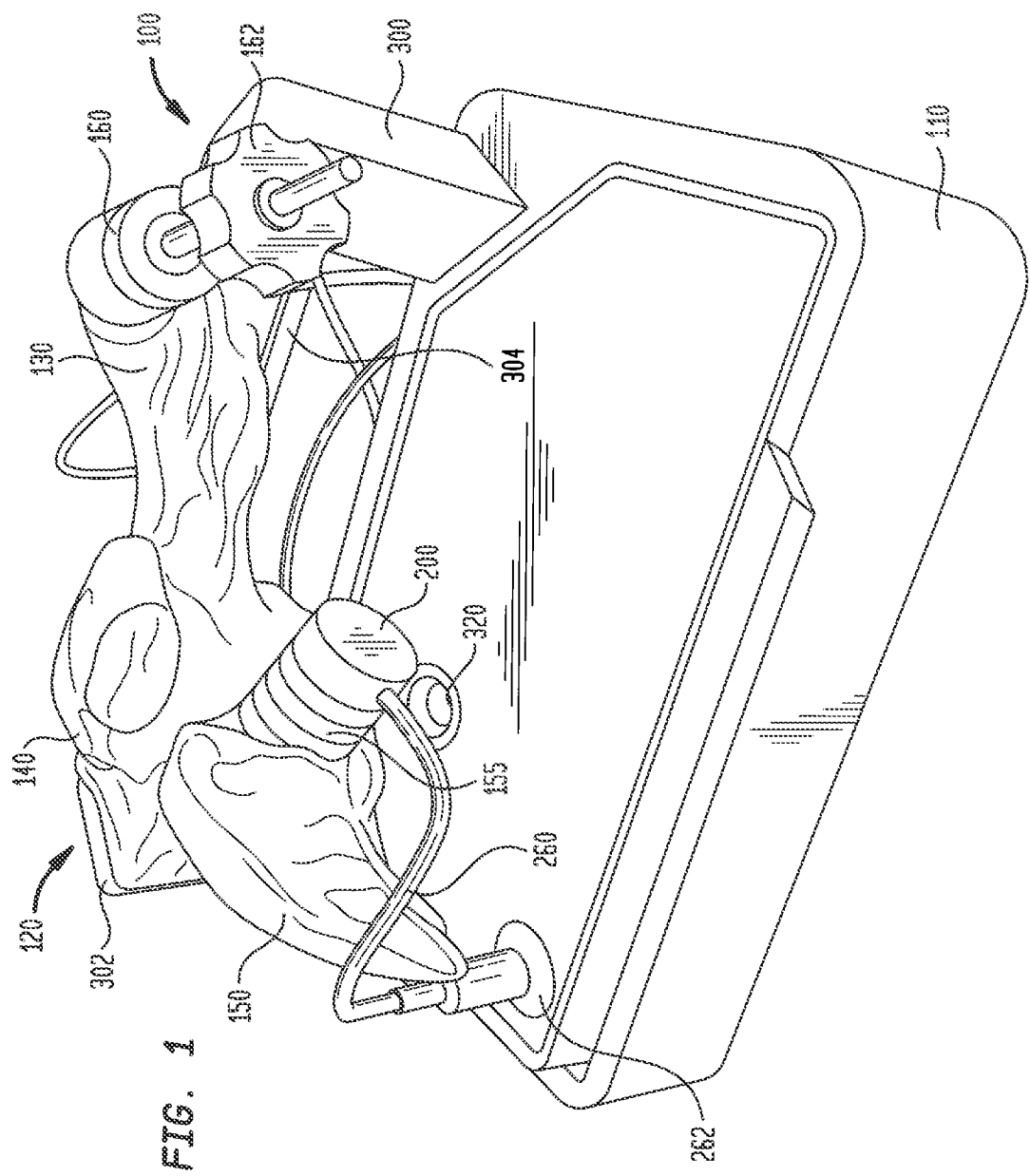
FIG. 1 is a perspective view of an electro-anatomical model according to the present disclosure, showing a plug insert and a port for inserting a delivery catheter and pacing lead into the model.
Figure 2:
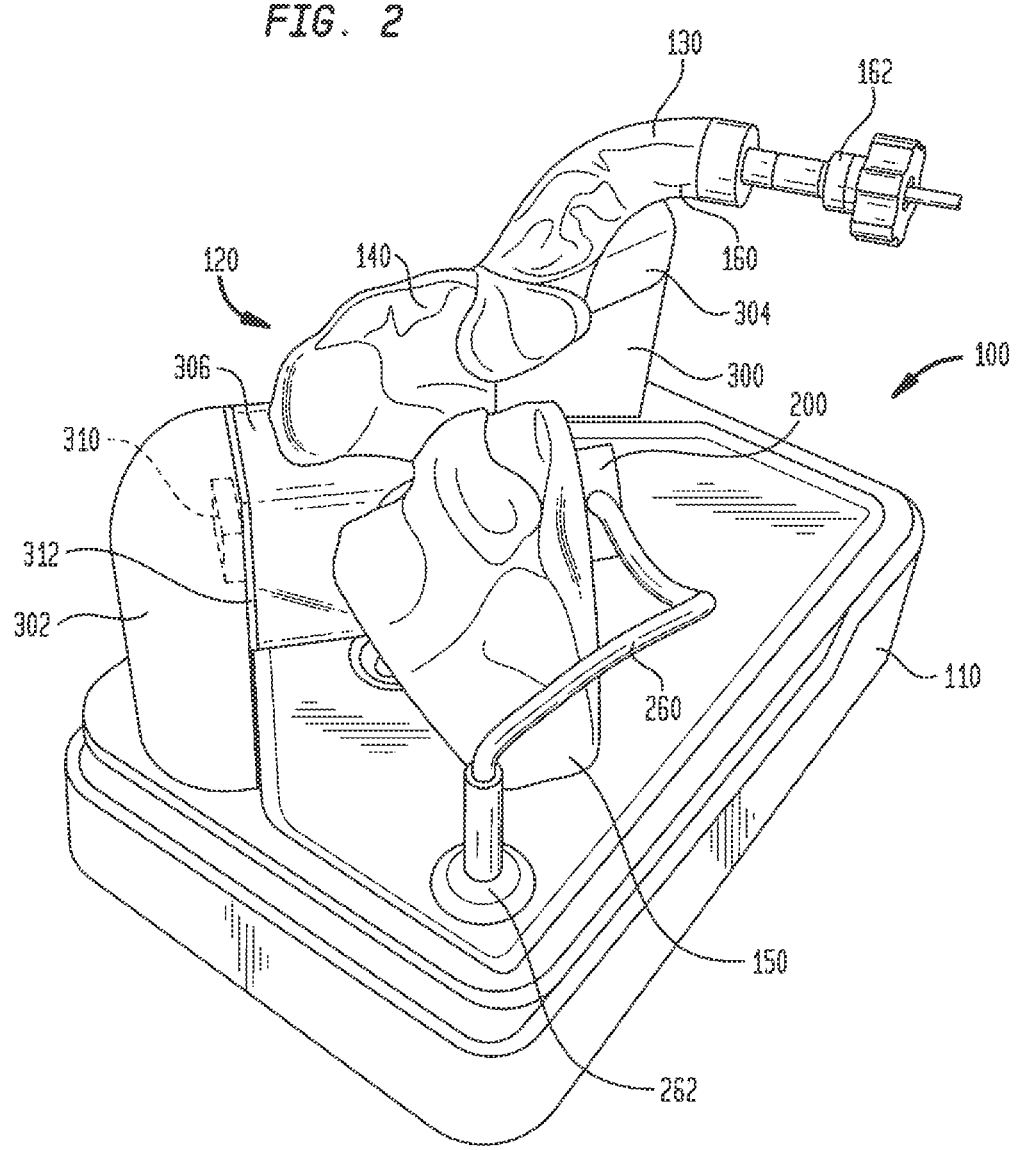
FIG. 2 is another perspective view of the electro-anatomical model of FIG. 1.
Figure 3:
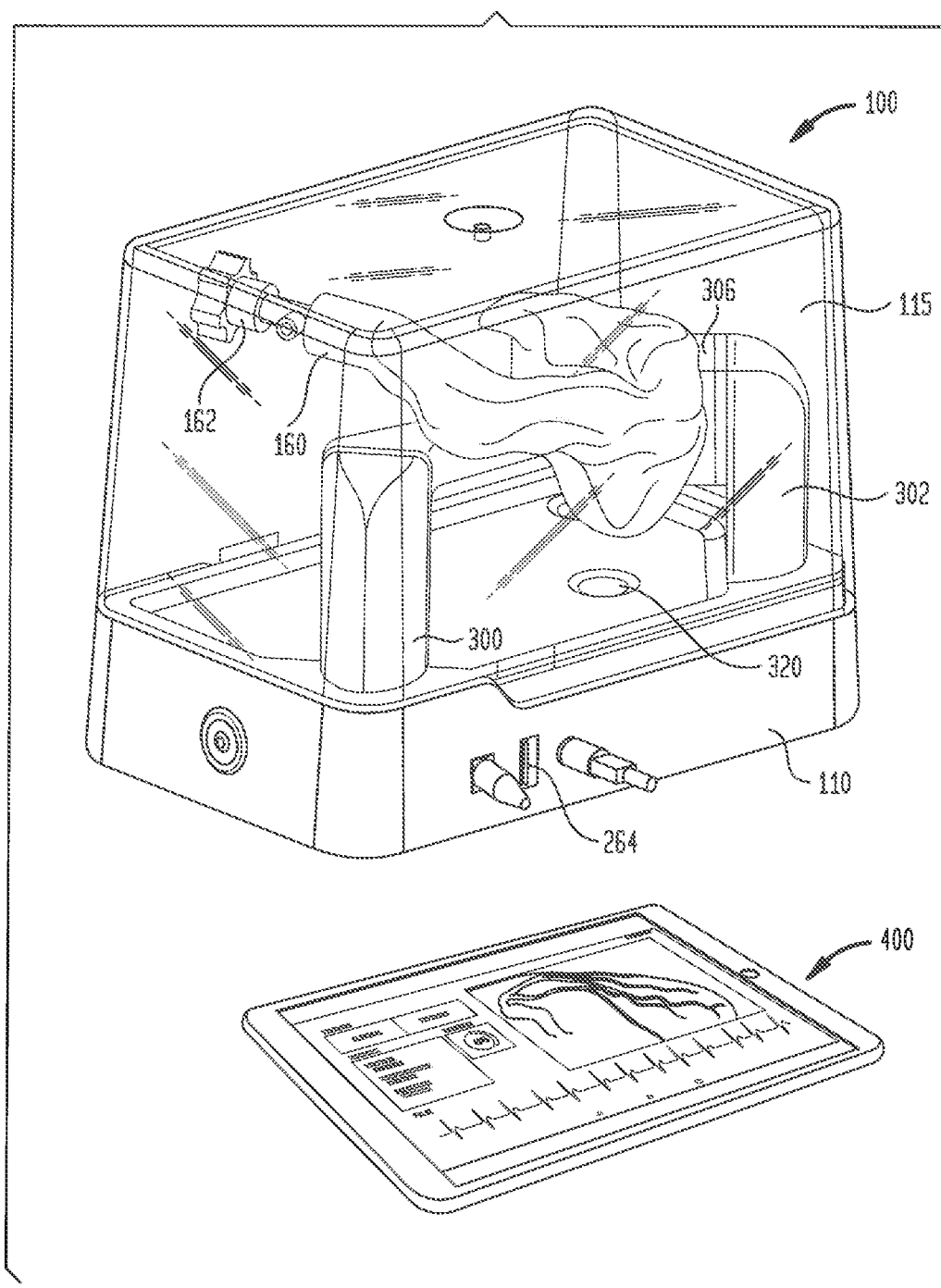
FIG. 3 is another perspective view of the electro-anatomical model of FIG. 1, along with a tablet for displaying images generated during use of the model.

An electro-anatomical model 100 according to the present disclosure is shown in FIGS. 1-3. Model 100 includes three main components, namely, an anatomically accurate shell 120, an electrically active plug insert 200, and a circuit for producing a simulated cardiac signal, such as the His signal.

Shell 120 is mounted on a base 110 that houses a circuit board for generating desired electrical signals, as well as other electronics for operating model 100. A removable cover 115 may mate with base 110 to cover shell 120 and protect same during shipment of model 100 and periods of nonuse. Shell 120 need only be as accurate as is needed for training or testing purposes. Thus, it need not look like, be oriented like, or be sized like the native anatomy so long as it is sufficiently anatomically accurate to permit its effective use. In one specific embodiment, as illustrated herein, shell 120 generally reproduces the anatomy of the right side of the human heart. Thus, referring to FIGS. 1-3, shell 120 includes a first portion 130 representing the superior vena cava, a second portion 140 representing the right atrium, and a third portion 150 representing the right ventricle. For convenience, these portions will be referred to herein by the anatomies they represent, i.e., superior vena cava 130, right atrium 140 and right ventricle 150. Each of these portions generally reproduces the anatomy on the inside, the outside, or both the inside and the outside of the structure it represents. As noted above, however, the actual anatomy is only reproduced to the extent needed. Therefore, for example, for purposes of the present disclosure in which model 100 is used to implant a pacing lead at the bundle of His, there is no need for a reproduction of the tricuspid valve between the right atrium and the right ventricle or other internal structures. Accordingly, these structures are not included in model 100.

Shell 120 is generally molded based on, for example, blood volume DICOM-based medical imaging, so it faithfully reproduces endocardial anatomy. Any other technique, such as casting, cutting from a blank, and the like, may also be used. And, as noted above, shell 120 need not be a faithful reproduction of specific anatomy—but it certainly can be.

Another technique which can be used to produce at least portions of shell 120 is 3D printing or additive manufacturing. There are many types of printing techniques and devices that can be employed depending on many factors including the size, shape and complexity of the item to be produced and the materials being used to produce them, all of which are known in the art. These techniques include, without limitation, material extrusion (e.g., fused filament fabrication/fused deposition modeling), vat polymerization (e.g., stereolithography/direct light processing), material jetting (e.g., drop on demand), binder jetting, powder bed fusion (e.g., selective laser sintering/direct laser sintering/selective laser melting/electron beam melting) and the like. Polymer, metal, ceramic and even biological structures and/or layers can be produced and imprinted using these techniques. The software for controlling the 3D printing process can be programmed based upon the medical imaging of the heart described above or through other noninvasive imaging techniques. The software may be modified to create non-anatomical structures, such as ports for plug insert 200, for other inserts, and for insertion of a delivery catheter or other tools into shell 120. Other modifications to the software can be made to create other structures, such as supports for shell 120, camera ports and other structures as needed.

Any material may be used to fabricate shell 120, but preferably the forming material is transparent and provides a rigid structure having sufficient structural integrity. Rather than being transparent, the forming material may be translucent, opaque or may prevent light transmission into or out from shell 120 altogether. Specific polymers useful for forming shell 120 include, without limitation, polylactic acids, acrylonitrile butadiene styrenes, nylons (polyamids such as PA6 from BASF and PA 11 and 12), high impact polystyrene, polyurethanes, polycarbonates, polyvinyl alcohols, polyimides (such as polyetherimides), polyaryletherketones (PAEK), polyether ether ketones (PEEK), high density polyethylenes, and the like. An example of a material useful for forming shell 120 is ACCURA 60 available from 3D Systems, Inc. of Rock Hill, S.C. Layers of cells may be created on any surface of shell 120 by 3D printing or other techniques to help provide a more realistic tactile and/or visual simulation. Metals may be used to imprint nerve-like structures or other features of the His/Purkinje system on any inner or outer surface or any layer of shell 120. In addition, a waterproofing material may be applied to the inner surface, the outer surface or both the inner and outer surface of shell 120 to help prevent the leakage of any fluid from the interior of the shell. One such waterproofing material may be a urethane clear coat available under the name SprayMax 3680061 from Peter Kwasny GmbH of the Federal Republic of Germany.

Shell 120 may include as much of the vasculature, atrial and/or ventricular anatomy as considered relevant. One or more ports may be made in shell 120 at positions representing possible locations of the bundle of His or at positions simulating the locations at which catheters and other tools typically enter the heart to access the bundle of His. These positions may be based on electrical maps taken as part of an electrophysiological study. A standardized shell can be used as a model or a custom shell can be generated for an individual patient based on his/her unique anatomy. In addition, as will be explained more fully below, ports may be made in shell 120 to accommodate a camera that provides visualization of plug insert 200. Other ports may be included, or other structures provided, to add light to the interior of model 100.

Referring to FIG. 1, a first port 155 may be provided in shell 120 for receiving plug insert 200. Port 155 is positioned near the intersection of right atrium 140 and right ventricle 150 at a location representing the typical location of the bundle of His. Port 155 has a generally cylindrical configuration, with a length and a diameter sized to receive plug insert 200 and to position an inside face thereof at or near the inner surface of shell 120 representing an inner surface of the heart.

Figure 4A:
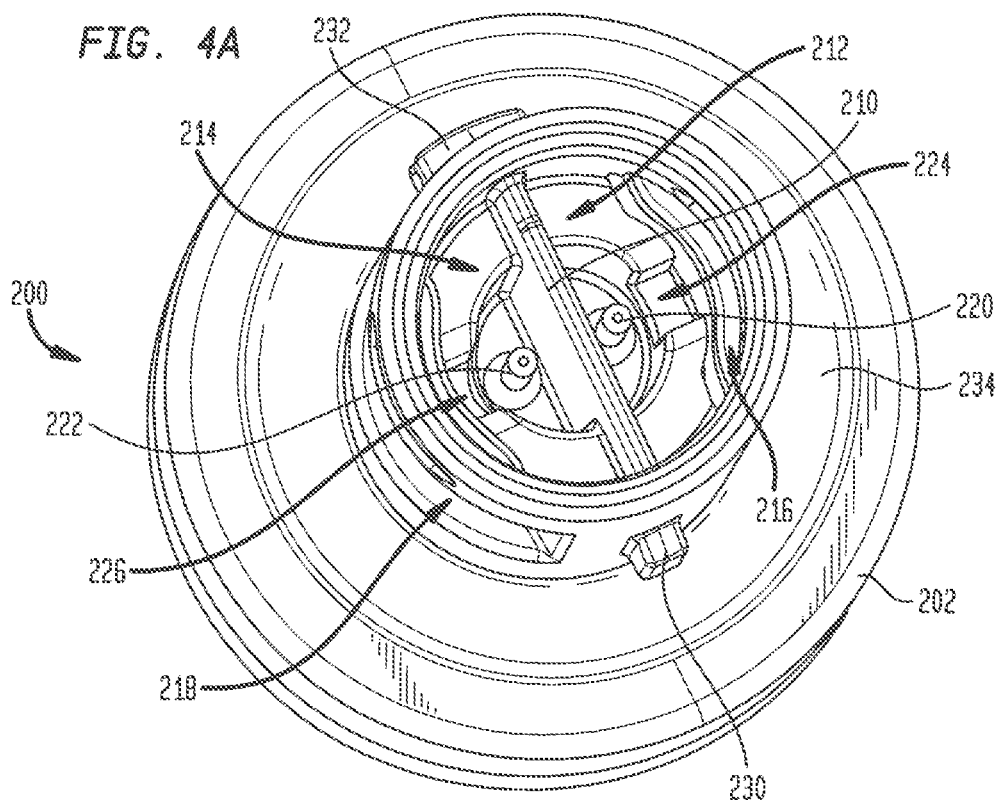
FIG. 4A is a top perspective view of a plug insert showing electrical connections and an electrical barrier.
Figure 4B:
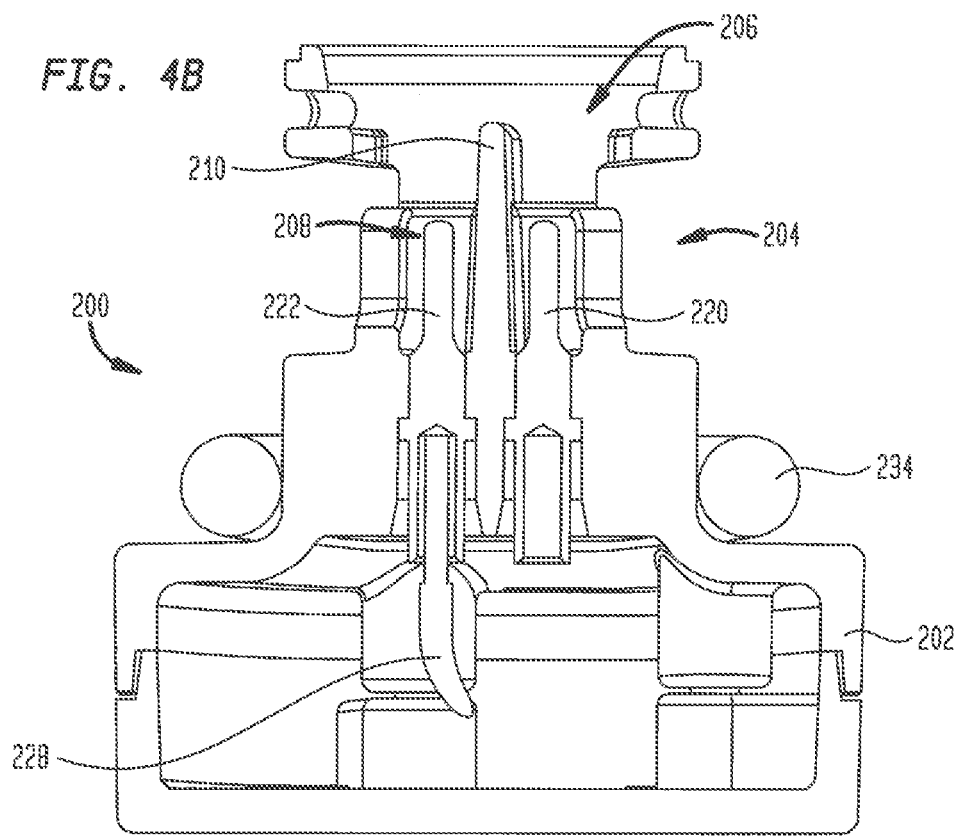
FIG. 4B is a longitudinal cross-section through the plug insert of FIG. 4A.
Figure 5A:
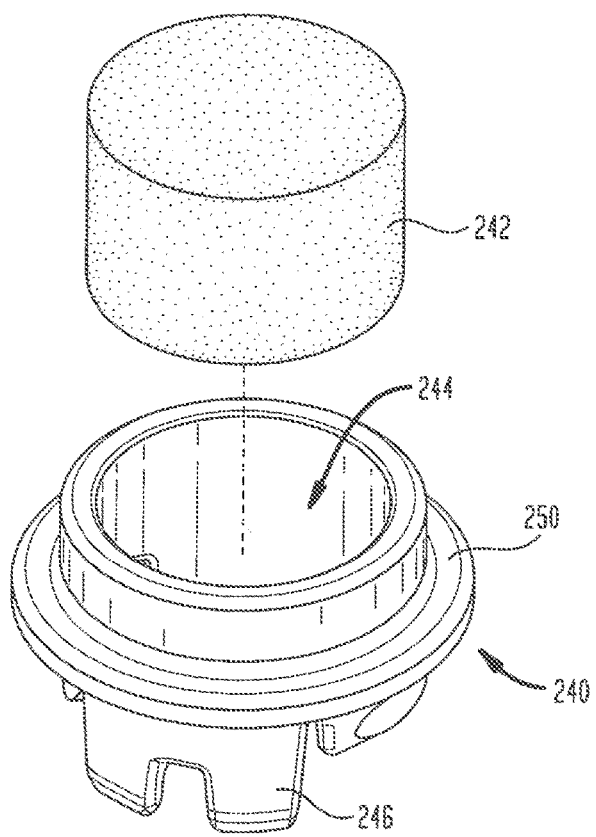
FIG. 5A is an exploded view of a carrier and a tissue analogue receivable in the carrier.
Figure 5B:
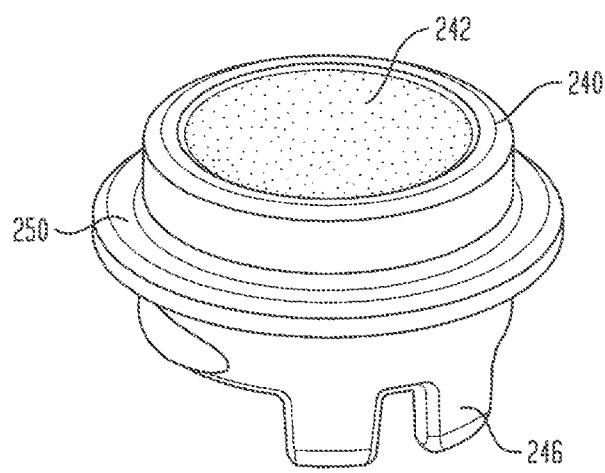
FIG. 5B is a top perspective view of the carrier of FIG. 5A with the tissue analogue assembled therein.
Figure 5C:
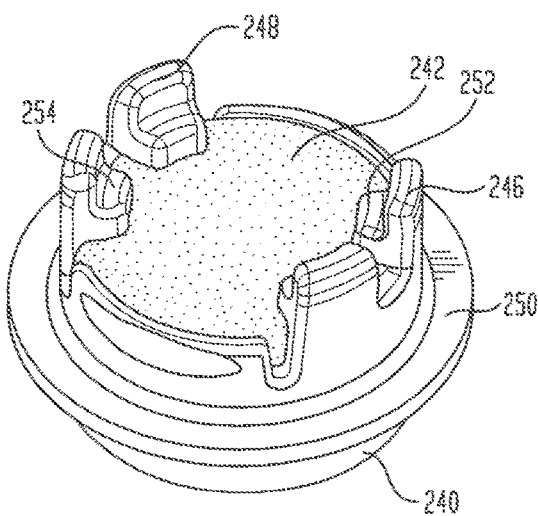
FIG. 5C is a bottom perspective view of the carrier of FIG. 5A with the tissue analogue assembled therein.

Referring to FIGS. 4A-4B, plug insert 200 has a base 202 and a generally cylindrical neck 204 extending away from the base. Neck 204 has a length and a diameter sized to be received in port 155, while base 202 has a larger diameter and is sized to reside outside of the port. A generally hollow cavity 206 is formed at the free end of neck 204, with a smaller hollow recess 208 formed between cavity 206 and base 202. A barrier 210 extends entirely across the diameter of recess 208 and across a lower portion of cavity 206, dividing recess 208 and the lower portion of cavity 206 into separate compartments 212 and 214. Elongated slots 216 and 218 in the outer wall of neck 204 provide fluid access to compartments 212 and 214, respectively. Plug insert 200 and barrier 210 are preferably formed from a strong, rigid, non-conductive material using any technique known in the art, including the forming techniques noted above for forming shell 120, and in particular molding and 3D printing. Barrier 210 may be formed integrally with plug insert 200, or may be formed separately and subsequently assembled to the plug insert. One example of a material for forming plug insert 200 and barrier 210 is VISIJET FLEX SL available from 3D Systems, Inc. Another strong, rigid, non-conductive polymer useful for forming plug insert 200 and barrier 210 is ABS plastic. Other useful materials will be readily apparent to those skilled in the art.

A first electrode 220 in plug insert 200 projects from base 202 upward into compartment 212, and a second electrode 222 projects upward from base 202 into compartment 214. This arrangement of electrodes 220 and 222 simulates the dipole electrical signal produced by the bundle of His. A channel 224 in compartment 212 provides a fluid path from slot 216 to electrode 220. Similarly, a channel 226 in compartment 214 provides a fluid path from slot 218 to electrode 222. A conductive wire 228 supplies a known electrical signal to electrode 222, while electrode 220 is connected to ground. A first shaped protrusion 230 is located on an outside surface of neck 204, and a second shaped protrusion 232 is located on the outside surface of neck 204 at a position diametrically opposed to protrusion 230. Protrusions 230 and 232 are sized and shaped to be received within corresponding channels (not shown) in the interior of port 155. Upon insertion of plug insert 200 into port 155, protrusions 230 and 232 engage with the corresponding port channels so that one quarter turn of the plug insert locks the plug insert to shell 120. Alternate arrangements for securely connecting plug insert 200 to port 155 are contemplated herein, including a threaded connection, a snap-fit connection, a friction fit connection and the like. An O-ring 234 assembled around neck 204 adjacent base 202 provides a fluid-tight seal between plug insert 200 and shell 120.

Plug insert 200 further includes a removable carrier 240 for receiving a plug 242 of a tissue analogue material. Carrier 240 has a generally ring-shaped structure with a central opening 244 therethrough. A first pair of legs 246 depends from one side of carrier 240 and a second pair of legs 248 depends from the carrier at a position diametrically opposed to legs 246. A first slot between legs 246 and a second slot between legs 248 are linearly aligned with one another and sized to receive an upper edge portion of barrier 210 when carrier 240 is inserted into cavity 206 in neck 204, thereby assuring the proper alignment of the carrier within plug insert 200. A rim 250 circumscribing the outer circumference of carrier 240 mates with a corresponding rim (not shown) at the inside end of port 155 to hold the carrier in place when plug insert 200 is assembled within the port.

Plug 242 has a cylindrical shape and is sized to fit within the opening 244 in carrier 240. In one embodiment, plug 242 may have a diameter of about 0.350 inches and a thickness of about 0.250 inches, although plugs having smaller or larger diameters and thicknesses are contemplated herein. Plug 242 is inserted into carrier 240 until a bottom surface thereof contacts stops 252 and 254 that project radially inwardly from each of legs 246 and 248, respectively. When fully inserted in carrier 240, the top surface of plug 242 is substantially coplanar with the top edge of the carrier. Carrier 240 is configured to enable plug 242 to be easily removed after use and replaced with a different plug of the same or a different material.

Plug 242 is formed from a material that simulates at least some of the physical and/or electrical properties of cardiac tissue in the vicinity of the bundle of His. In particular, the analogue material is relatively soft (compared to shell 120) to simulate the force required to implant a pacing lead into cardiac tissue and to retain the pacing lead in the cardiac tissue once implanted. Preferably, the analogue material also is capable of ion conduction so that electrical signals entering compartment 214 through electrode 222 can be conducted through plug 242 to compartment 212 and electrode 220 therein. One material that exhibits all of these properties is a soft, flexible, open-cell polyurethane foam, such as the type that may be used in air filters. The open cells in the foam are able to absorb the fluid within shell 120, producing a conductive path from compartment 214 to compartment 212. Moreover, the foam has sufficient integrity that it is able to be reused multiple times.

Shell 120 may also include a second port 160 for inserting catheters and other tools into the interior of the shell. Since the bundle of His is typically accessed through the superior vena cava, port 160 is positioned at an entrance to superior vena cava 130 of model 100. A conventional tuohy-borst hemostatic valve 162 may be assembled to port 160 through threaded engagement or other connection to minimize the leakage of fluid through port 160 as tools are inserted therethrough and to simulate the resistance encountered as a catheter or other tool travels through an introducer sheath into the heart and toward the bundle of His. Other forms of hemostatic valves or other inserts may be assembled in port 160. Depending on the shape of the shell and its intended use, the shell may be provided with one or more additional ports and inserts at desired locations.

Shell 120 is mounted to base 110 by a pair of stanchions 300 and 302. Stanchion 300 may support shell 120 near superior vena cava 160. In that regard, a structural support arm 304 may be integrally formed with shell 120 and may extend outwardly from the shell for connection to stanchion 300. Support arm 304 may be hollow, but preferably is not in fluid communication with the interior of shall 120.

Stanchion 302, on the other hand, may support shell 120 at the junction of right atrium 140 with right ventricle 150, in a position opposite port 155. A large structural support arm 306 may be integrally formed with shell 120 and may extend therefrom for connection to stanchion 302. Support arm 306 may be hollow, but preferably is not in fluid communication with the interior of shell 120. Stanchion 302 may include a video camera 310 that provides a line of sight image of port 155 and plug insert 200 therein. A source of illumination, such as LED lights 312 may be connected to stanchion 302 for illuminating the face of plug 242 and the surrounding area so that efforts to locate the simulated bundle of His and implant a pacing lead therein may be viewed through camera 310. Electrical connections to camera 310 and LED lights 312 may travel through stanchion 302 for connection to the circuitry in base 110. Preferably, shell 120 is mounted to stanchions 300 and 302 such that superior vena cava 130 is the highest point of the shell. This orientation helps prevent fluid within shell 120 from leaking out from the shell through the superior vena cava.

Model 100 may include a second video camera 320 mounted in base 110 directly below the exposed face of plug 242. Video camera 320 may be of the same type as video camera 310. Video camera 320 provides an image of the location of the simulated bundle of His that mimics the fluoroscopic image of the heart obtained during an actual procedure. Although camera 320 may be a color video camera, the image captured by the camera is converted to black and white and, since the image is being obtained from below the simulated bundle of His rather than from above the actual bundle of His in an actual procedure, the image is inverted left to right. These manipulations of the image from camera 320 create an image that more closely mimics an actual fluoroscopic image of the heart.

During the use of model 100, the interior of shell 120 is filled with a fluid. The type of fluid will depend upon what the model is being used for. When model 100 is being used to develop tools for locating the bundle of His and inserting a pacing lead therein, or when the model is being used to teach techniques for performing these procedures, shell 100 is filled with a conductive fluid. Any electrically conductive material in solution, suspension, or in particulate form can be used to provide electric conductivity. Such materials include common salts of halogens, as well as salts of potassium, calcium, magnesium, and phosphorus. A particularly preferred conductive fluid is distilled water to which sodium chloride has been added to produce a solution having a repeatable degree of conductivity. One example of such solution may include three parts deionized water to one part of a 0.9N (normal) saline solution, although the exact ratio of ingredients is not critical.

To use model 100 to locate the bundle of His and insert a pacing lead therein, a plug 242 of an appropriate tissue analog material, such as the open-cell polyurethane foam discussed above, is inserted into carrier 240, and the carrier is then inserted into cavity 206 at the free end of plug insert 200. Plug insert 200 may then be inserted into first port 155 and turned to lock the plug insert in place in the port. The interior of shell 120 may then be filled with a conductive fluid, such as a distilled water/sodium chloride solution. A sufficient amount of the solution is added to at least cover port 155 so that the solution fills cavity 206 and recess 208 in plug insert 200 and permeates the pores in foam plug 242. An electrical lead 260 extending from the base 202 of plug insert 200 may be inserted into a receptacle 262 in base 110 to provide an electrical connection between the circuitry in base 110 and the electrodes 220 and 222 in plug insert 200. A computer tablet 400 may be connected to an input jack 264 in base 110 for displaying the images from cameras 310 and 320, the electrical signals detected by a pacing lead and/or an introducer catheter, as well as other parameters input or output from model 100. The computer tablet 400 may also be used to control the operation of model 100, such as the operation of lights 312 and the shape and intensity of the electrical signal sent to electrode 222.

Model 100 may be turned on by actuating an on/off switch (not shown) on base 110. This causes the circuitry in base 110 to generate an electric signal that simulates the signal produced by the bundle of His. This circuitry may include a single-board computer running custom software to generate realistic electrophysiological signals. The circuitry may also include a bipolar amplifier capable of driving symmetric (positive and negative) voltages into impedences of at least a few hundred ohms at levels of up to 4 volts. The output of the computer is an accurate voltage of limited range (about 0.55 volts to about 2.8 volts), which the amplifier amplifies to a symmetric output of +/−4 volts. Any other circuitry which can generate an output that is sufficiently analogous to the electrical potential generated by the bundle of His in vivo may be used, including an asymmetric amplifier coupled through a large capacitor. In any event, the signal output by the circuitry is conducted through electrical lead 260 to electrode 222 in plug insert 200. The conductive fluid in recess 208, cavity 206, and in the open pores in plug 242 will conduct the signal from compartment 214 over non-conductive barrier 210 to the electrode 220 in compartment 212. As the electric signal passes over barrier 210, it will be close to the exposed face of plug 242 where it may be received by the electrodes of an introducer catheter.

Figure 6:
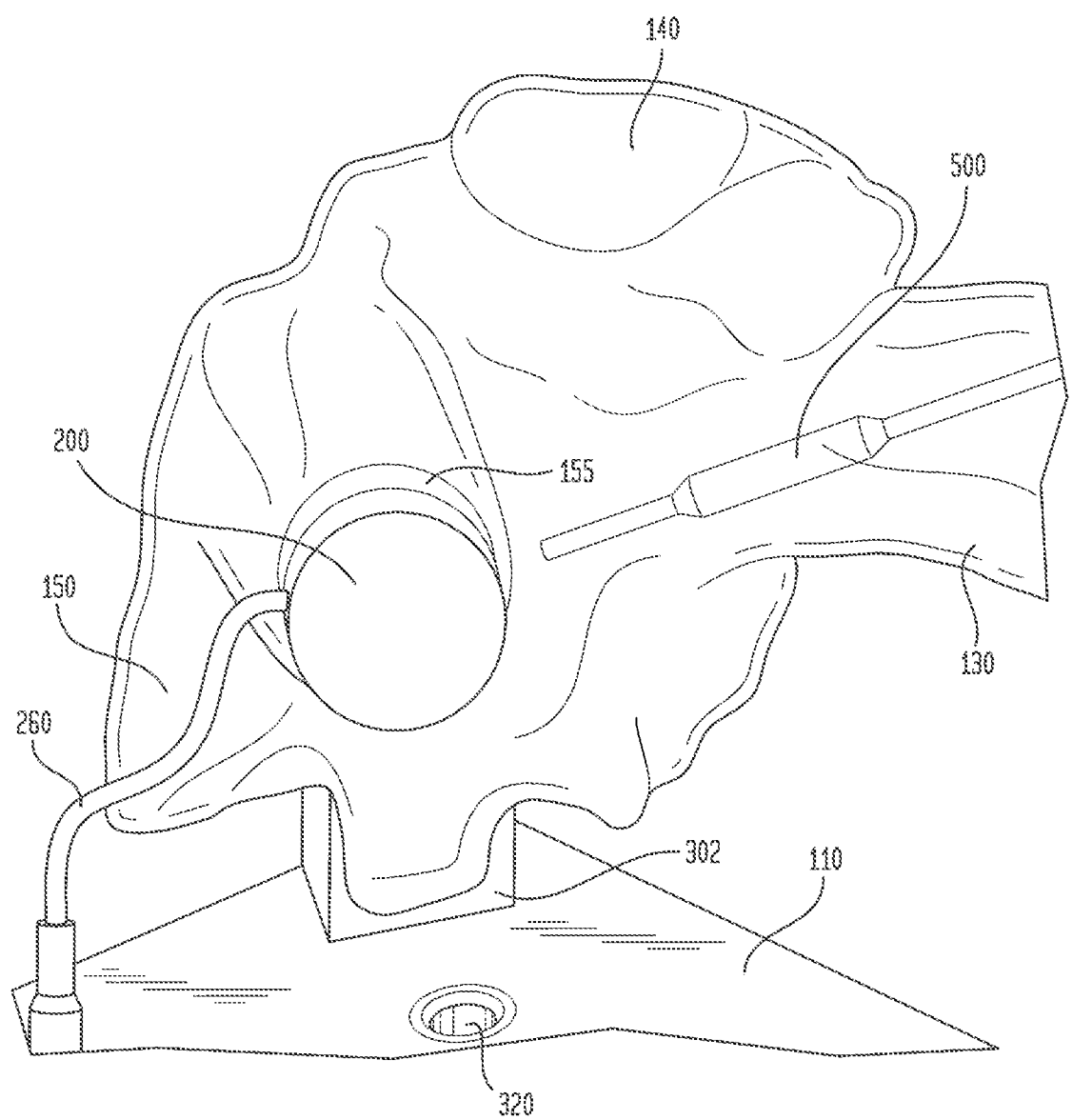
FIG. 6 is a partial view of the electro-anatomical model of FIG. 1 showing an introducer catheter therein for locating the bundle of His and inserting a pacing lead therein.

An introducer catheter 500 may be inserted through hemostatic valve 162 into superior vena cava 130 and maneuvered through the superior vena cava to the right atrium 140, as generally illustrated in FIG. 6. The introducer catheter may have a sheath with an axial lumen, a distal end, at least one electrode at the distal end, and a pacing lead disposed in the axial lumen. The user may maneuver the distal end of catheter 500 toward the exposed face of plug 242, and may monitor the advancement of the catheter near port 155 through images from cameras 310 and 320 displayed on computer tablet 400. As the distal end of catheter 500 nears and confronts the face of plug 242, at least a portion of the electrical signals generated by model 100 in simulating those emanating from the bundle of His will be detected by the at least one electrode in the catheter. At this juncture, the user will know that the distal end of catheter 500 is aligned with the simulated bundle of His. If catheter 500 does not receive electrical signals, or if the signals received are very faint, the user may maneuver the distal end of catheter 500 to scan the exposed face of plug 242. When the signals received by catheter 500 are the strongest, the user can be confident that the simulated His bundle has been located. At this point, the pacing lead (not shown) can be implanted in foam plug 242 by advancing the helical fixation anchor of the lead out from the axial lumen of catheter 500 and rotating the lead to drive the fixation anchor into the foam plug.

Figure 7A:
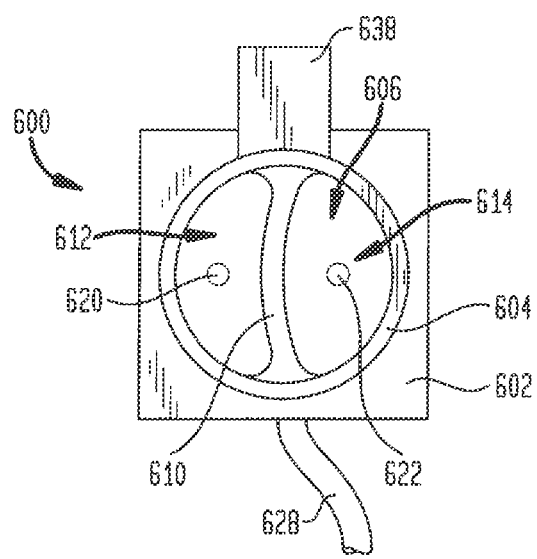
FIG. 7A is a top view of an empty plug insert according to another embodiment of the present disclosure, showing electrical connections and an electrical barrier.
Figure 7B:
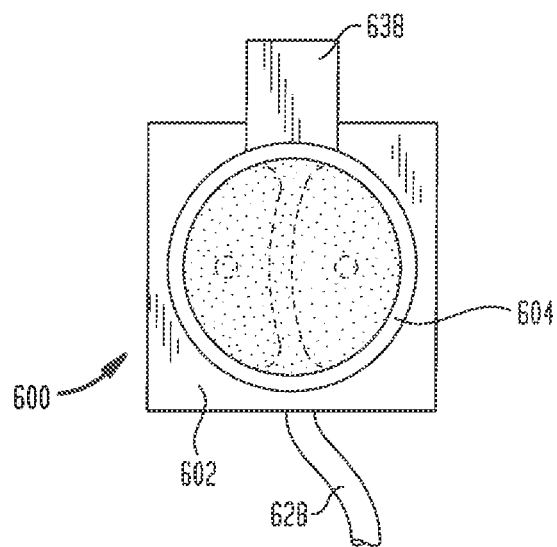
FIG. 7B is a top view of the plug insert of FIG. 7A filled with a conductive gel.
Figure 8:
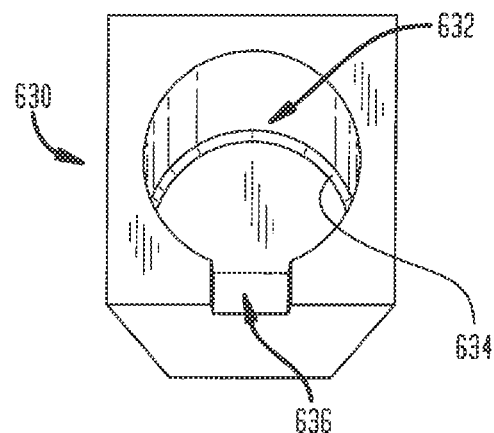
FIG. 8 is a bottom perspective view of a contoured cap for forming a surface of the plug insert of FIG. 7B.
Figure 9:
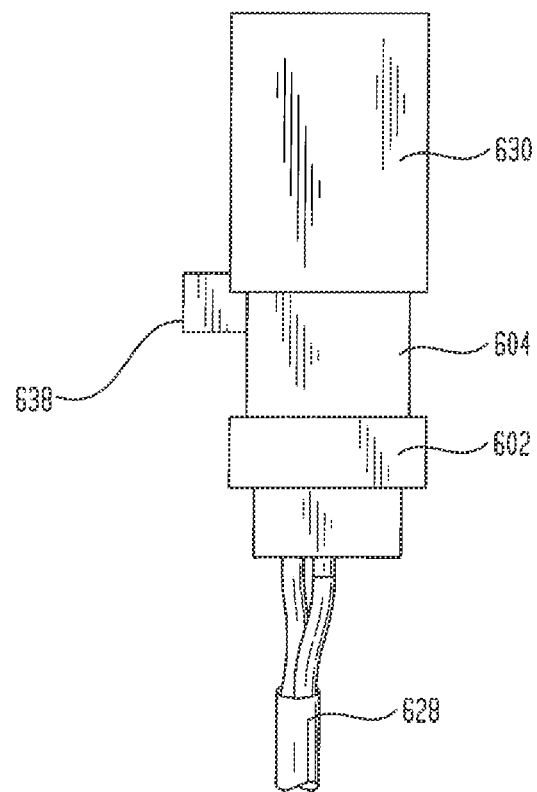
FIG. 9 is a side elevational view of the plug insert of FIG. 7B and the contoured cap of FIG. 8 in assembled relationship.

Although model 100 has been described above as including a plug insert 200 with a removable carrier and a plug 242 of a polyurethane foam tissue analogue material, other structures for simulating cardiac tissue and the electrical signals generated by the bundle of His are possible. For example, in another embodiment hereof, plug insert 200 may be replaced with a gel plug insert 600. Referring to FIGS. 7A-7B, gel plug insert 600 has a generally square or rectangular base 602 and a generally cylindrical neck 604 extending away from the base. Neck 604 has a length and diameter sized to be received in port 155 while the cross-section of base 602 is larger than that of neck 604 and intended to reside outside of the port. Neck 604 has a generally hollow interior 606, with a barrier 610 extending upward from base 602 and dividing the interior into separate compartments 612 and 614. The base 602 and neck 604 of gel plug insert 600 may be formed from a strong, rigid, non-conductive polymer using any technique known in the art, including the forming techniques noted above, and in particular 3D printing. Examples of materials from which gel plug insert 600 may be formed include VISIJET FLEX SL available from 3D Systems, Inc. and ABS plastic, among others. Barrier 610, on the other hand, is preferably formed from a semi-rigid or pliable, non-conductive polymer. Accordingly, barrier 610 is formed separately from the base 602 and neck 604 of gel plug insert 600 and is subsequently assembled in the interior 606 of the neck. Barrier 610 may be formed using any suitable technique known in the art, including 3D printing. Gel plug insert 600 includes a first electrode 620 that projects from base 602 upward into compartment 612, and a second electrode 622 that projects upward from base 602 into compartment 614. A conductive wire 628 supplies a known electrical signal to electrode 622, while electrode 620 is connected to ground.

The interior 606 of neck 604 may be filled with a substance that simulates the electrical and/or physical properties of cardiac tissue. In one embodiment, the substance may be a gel. The gel may be a mixture of gelatin and saline, which renders the gel electrically conductive, and may also contain a cross-linking agent to modify the physical properties of the gel. Any type of natural or synthetic gel may be used so long as it provides the desired physical and/or electrical properties. A porcine gelatin, for example, may be used. The gel preferably has a viscosity sufficient to simulate the physical properties of the relevant tissue, and has sufficient structural integrity that it does not flow, ooze or provide a tacky residue. In one embodiment, the gel may have a SHORE 00 hardness of at least about 10, and more preferably, at least about 30. One example of an appropriate conductive gel may be formed from 50 gm of porcine gelatin powder, 30 ml of deionized water, and 10 ml of 0.9N saline, although the exact ratio of ingredients is not critical. Neck 604 may be filled with substances other than a gel so long as the substance simulates the electrical and/or physical properties of cardiac tissue.

With barrier 610 in place in neck 604 so as to divide the interior 606 of the neck into compartments 612 and 614, the interior of the neck may be filled with the gel in liquid form so that the gel covers barrier 610. Before the gel cures to a solid (but pliable) state, a layer of a fibrous mesh, loosely woven fabric, foam or other material may be placed over the gel at the open end of neck 604. An example of a suitable material is cheesecloth. This material layer more accurately simulates the friability of myocardial tissue so as to more realistically simulate the retention of a pacing lead in tissue. With the material layer in place, a cap 630 is assembled over the open end of neck 604. Cap 630 has a recess 632 at one end that is sized to snuggly fit over the open end of neck 604. The closed end of recess 632 may be contoured to match the interior contour of shell 120 adjacent port 155 so that, with gel plug insert 600 in place in the port, the exposed surface of the gel and the interior surface of the shell will together approximate a continuous surface. An annular channel 634 may be formed around the bottom of recess 632 to receive the free end of neck 604 so that the contoured surface can be inserted slightly into the free end of the neck to mold the shape of the gel surface. Cap 630 may be formed using the same techniques and the same materials described above for forming the base 602 and neck 604 of gel plug insert 600. To assure the proper alignment of contoured cap 630 on the neck 604 of gel plug insert 600, the bottom edge of the cap includes a notch 636 that mates with a corresponding lug 638 on the outside surface of neck 604.

Once the gel in gel plug insert 600 has set, cap 630 may be removed therefrom and the plug insert may be inserted into port 155 of model 100. Although not shown, the outside surface of the neck 604 of gel plug insert 600 may include shaped protrusions that are the same as or similar to protrusions 230 and 232 described above in connection with plug insert 200. These protrusions may be sized and shaped to be received within corresponding channels in the interior of port 155. Upon insertion of gel plug insert 600 into port 155, the protrusions may engage with the corresponding port channels to lock the plug insert to shell 120. Alternate arrangements for securely connecting gel plug insert 600 to port 155 are contemplated herein, including a threaded connection, a snap-fit connection, a friction fit connection and the like. With gel plug insert 600 in place in port 155, model 100 may be operated in the same manner as described above to locate the bundle of His and insert a pacing lead therein. However, rather than having the electrical signals travel from one electrode to the other electrode through the conductive fluid in cavity 206, recess 208 and the open porosity in foam plug 242 as with plug insert 200, the electrical signals in gel plug insert 600 travel from one electrode to the other electrode through the conductive gel.

Other variants of model 100 are also contemplated herein. For example, it may be desirable to highlight all or a portion of model 100 when performing certain procedures. This may be accomplished by including a fluorescent substance in the material forming a target portion or portions of shell 120. Alternatively, after shell 120 has been formed, a fluorescent substance may be applied to the inside and/or outside surface of the shell at the target portion or portions. As a still further alternative, a fluorescent substance may be added to the conductive fluid added to shell 120 to highlight the entire contents. Those areas of model 100 that include the fluorescent substance may fluoresce under ultraviolet light.

In yet another variant, the model of the present disclosure may be fabricated to simulate certain structures of a beating heart. In such arrangement, the shell of the model may be formed from a pliable material, such as silicone, using any of the fabrication techniques described above. The model may include one or more internal structures, such as the interatrial septum, interventricular septum, one or more cardiac valves and the like. The shell may be filled with a conductive fluid in fluid communication with a pump that produces a pulsatile pressure change. Operation of the pump at a desired pumping speed may then simulate the beating of the heart. In certain embodiments, glycerol or other agents may be added to increase the viscosity of the conductive fluid in the shell to better simulate the viscosity of blood.

Although the model according to the present disclosure has been described in connection with its use to simulate the electrical signals emanating from the bundle of His and the physical and/or electrical properties of the cardiac tissue associated with same for the purpose of developing clinical tools to facilitate His pacing and enabling the training of users on the implantation of His pacing leads, other uses of the model or of other anatomical models are also contemplated herein. For example, appropriate anatomical models may be useful for sensing atrioventricular nodes, for isolating the pulmonary vein, or for implanting a right ventricular apex lead. Still other models may be useful for simulating the electrical signals associated with, for example, an atrial contraction, a ventricular contraction or a coronary sinus.

To summarize the foregoing, a first aspect of the disclosure provides an electro-anatomical model of the mammalian His/Purkinje system. The model includes a base; a shell mounted to the base and simulating the anatomy of at least a portion of a mammalian heart, the shell having a hollow interior; a first port providing an aperture to the interior of the shell; a plug inserted in the first port, the plug having a surface exposed to the interior of the shell; and a circuit providing electrical signals to the plug to simulate electrical signals generated by the bundle of His/Purkinje system in vivo; and/or the portion of the mammalian heart may include the right atrium and the right ventricle of the heart; and/or
the portion of the mammalian heart may further include a portion of the superior vena cava; and/or
the shell may be coated with a waterproofing composition; and/or
the waterproofing composition may be coated on an exterior surface of the shell and on an interior surface of the shell; and/or
the shell may include a second port providing access for a tool to enter the interior of the shell; and/or
the second port may include a hemostasis valve; and/or
the exposed surface of the plug may include a material insert simulating tissue of the mammalian heart; and/or
the material insert in use may be electrically conductive; and/or
the material insert may have a structure including open porosity; and/or
the material insert may include a porous polyurethane foam; and/or
the material insert may include a conductive gel; and/or
the plug may include a first electrode connected to the circuit and a second electrode connected to ground, the first electrode being separated from the second electrode; and/or
the plug may include a physical barrier disposed between the first electrode and the second electrode; and/or
the exposed surface of the plug may include a material insert simulating tissue of the mammalian heart, the material insert providing a conductive path between the first electrode and the second electrode; and/or
the interior of the shell may include a conductive fluid, the conductive fluid conducting electrical signals from the first electrode to the second electrode; and/or
the model may further include a first video camera for capturing images at the exposed surface of the plug; and/or
the shell may be mounted to the base by a plurality of stanchions, the first video camera being mounted in one of the stanchions in alignment with the exposed surface of the plug; and/or
the model may further include a second video camera mounted in the base and adapted to capture images in the vicinity of the exposed surface of the plug.

A second aspect of the disclosure provides a method for simulating the delivery of a pacing lead to the His bundle of a patient's heart. The method includes providing an electro-anatomical model simulating the anatomy of at least a portion of a mammalian heart, the model including a shell with a hollow interior, first and second ports providing apertures to the interior of the shell, and a plug inserted in the first port, the plug having a face exposed to the interior of the shell; transmitting electrical signals to the plug to simulate electrical signals generated by the bundle of His/Purkinje system in vivo; providing an introducer catheter having a sheath with an axial lumen, a distal end, an electrode at the distal end, and a pacing lead disposed in the axial lumen; inserting the introducer catheter through the second port to the interior of the shell until the distal end of the sheath confronts the exposed face of the plug; moving the distal end of the sheath relative to the exposed face of the plug until the electrode at the distal end of the sheath receives at least a portion of the electrical signals transmitted to the plug; and deploying the pacing lead from the axial lumen of the sheath and implanting the pacing lead in the exposed face of the plug.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An electro-anatomical model of the mammalian His/Purkinje system, the model comprising:
   a base;
   a shell mounted to the base and simulating the anatomy of at least a portion of a mammalian heart, the shell having a hollow interior;
   a first port providing an aperture to the interior of the shell;
   a plug inserted in the first port, the plug having a surface exposed to the interior of the shell; and
   a circuit providing electrical signals to the plug to simulate electrical signals generated by the bundle of His/Purkinje system in vivo.

2. The electro-anatomical model as claimed in claim 1, wherein the portion of the mammalian heart includes the right atrium and the right ventricle of the heart.

3. The electro-anatomical model as claimed in claim 2, wherein the portion of the mammalian heart further includes a portion of the superior vena cava.

4. The electro-anatomical model as claimed in claim 1, wherein the shell is coated with a waterproofing composition.

5. The electro-anatomical model as claimed in claim 4, wherein the waterproofing composition is coated on an exterior surface of the shell and on an interior surface of the shell.

6. The electro-anatomical model as claimed in claim 1, wherein the shell includes a second port providing access for a tool to enter the interior of the shell.

7. The electro-anatomical model as claimed in claim 6, wherein the second port includes a hemostasis valve.

8. The electro-anatomical model as claimed in claim 1, wherein the exposed surface of the plug includes a material insert simulating tissue of the mammalian heart.

9. The electro-anatomical model as claimed in claim 8, wherein the material insert in use is electrically conductive.

10. The electro-anatomical model as claimed in claim 9, wherein the material insert has a structure including open porosity.

11. The electro-anatomical model as claimed in claim 8, wherein the material insert comprises a polyurethane foam.

12. The electro-anatomical model as claimed in claim 8, wherein the material insert comprises a conductive gel.

13. The electro-anatomical model as claimed in claim 1, wherein the plug includes a first electrode connected to the circuit and a second electrode connected to ground, the first electrode being separated from the second electrode.

14. The electro-anatomical model as claimed in claim 13, wherein the plug includes a physical barrier disposed between the first electrode and the second electrode.

15. The electro-anatomical model as claimed in claim 14, wherein the exposed surface of the plug includes a material insert simulating tissue of the mammalian heart, the material insert providing a conductive path between the first electrode and the second electrode.

16. The electro-anatomical model as claimed in claim 13, wherein the interior of the shell includes a conductive fluid, the conductive fluid conducting electrical signals from the first electrode to the second electrode.

17. The electro-anatomical model as claimed in claim 1, further comprising a first video camera for capturing images at the exposed surface of the plug.

18. The electro-anatomical model as claimed in claim 17, wherein the shell is mounted to the base by a plurality of stanchions, the first video camera being mounted in one of the stanchions in alignment with the exposed surface of the plug.

19. The electro-anatomical model as claimed in claim 17, further comprising a second video camera mounted in the base and adapted to capture images in the vicinity of the exposed surface of the plug.

20. A method for simulating the delivery of a pacing lead to the His bundle of a patient's heart, the method comprising:
   providing an electro-anatomical model simulating the anatomy of at least a portion of a mammalian heart, the model including a shell with a hollow interior, first and second ports providing apertures to the interior of the shell, and a plug inserted in the first port, the plug having a face exposed to the interior of the shell;
   transmitting electrical signals to the plug to simulate electrical signals generated by the bundle of His/Purkinje system in vivo;
   providing an introducer catheter having a sheath with an axial lumen, a distal end, an electrode at the distal end, and a pacing lead disposed in the axial lumen;
   inserting the introducer catheter through the second port to the interior of the shell until the distal end of the sheath confronts the exposed face of the plug;
   moving the distal end of the sheath relative to the exposed face of the plug until the electrode at the distal end of the sheath receives at least a portion of the electrical signals transmitted to the plug; and
   deploying the pacing lead from the axial lumen of the sheath and implanting the pacing lead in the exposed face of the plug.

* * * * *